(12) United States Patent
Atherton

(10) Patent No.: US 7,002,340 B2
(45) Date of Patent: Feb. 21, 2006

(54) METHOD FOR INSPECTING PRESTRESSED CONCRETE PRESSURE PIPES BASED ON REMOTE FIELD EDDY CURRENT/TRANSFORMER COUPLING AND USE OF NON-COAXIAL COILS

(76) Inventor: David L. Atherton, 2021 Morrison Road, RR#2 Perth Road, ON (CA) K0H 2L0

( * ) Notice: Subject to any disclaimer, the term of this patent is extended or adjusted under 35 U.S.C. 154(b) by 212 days.

(21) Appl. No.: 10/395,244

(22) Filed: Mar. 25, 2003

(65) Prior Publication Data
US 2004/0189289 A1  Sep. 30, 2004

(51) Int. Cl.
*G01N 27/82* (2006.01)
(52) U.S. Cl. .................................... 324/220; 324/240
(58) Field of Classification Search ............... 324/219, 324/220, 221, 228, 230–243; 340/673, 676
See application file for complete search history.

(56) References Cited

U.S. PATENT DOCUMENTS

| | | | | |
|---|---|---|---|---|
| 3,651,506 A | * | 3/1972 | Olaf et al. .................. | 340/676 |
| 3,834,524 A | * | 9/1974 | Ratz et al. ............. | 198/810.02 |
| 4,797,613 A | * | 1/1989 | Wentzell ..................... | 324/220 |
| 4,806,863 A | * | 2/1989 | White ......................... | 324/238 |
| 4,814,702 A | * | 3/1989 | Driggers et al. ........ | 324/207.22 |
| 5,168,266 A | * | 12/1992 | Fukuda ....................... | 340/676 |
| 6,127,823 A | | 10/2000 | Atherton | |

FOREIGN PATENT DOCUMENTS

WO   WO 02/061412 A2   8/2002

OTHER PUBLICATIONS

Remote Field Eddy Current Inspection. D.L. Atherton. IEEE Trans on Magnetics vol. 31 No. 6 Nov 1995.
Detecting Breaks in prestressing pipe wire, D.L. Atherton et al, Journal AWWA vol. 92, Issue 7, Jul. 2000.
Finite Element Calculations for shields in remote-field Eddy Current Tools, D.L. Atherton et al. Materials Evaluation 47, Sept 1989, 1084-1088.
Effect of Shielding and Exciter Coil Tilt on the Remote-Field Effect, von Rosen et al, Materials Evaluation Jan 1993, 66-71.

\* cited by examiner

*Primary Examiner*—Jay Patidar

(57) ABSTRACT

A method for detecting breaks in a prestressed wire, rod or bar in prestressed concrete pressure pipe (PCCP), embedded in concrete and/or mortar is described. A remote field eddy current exciter/transformer coupling probe is traversed axially internally through the PCPP so as to create an energy flow path within and external to the wall of the PCPP and to induce a transformer coupling from the prestressing winding thus generating a signal in a detector spaced from and usually approximately coplanar with the exciter. As the exciter traverses a break in the wire, rod or bar, a small signal change is generated in the detector, nearly regardless but not independent of the radial position of the detector relative to the break.

22 Claims, 4 Drawing Sheets

METHOD FOR INSPECTING PRESTRESSED CONCRETE PRESSURE PIPES BASED ON REMOTE FIELD EDDY CURRENT/TRANSFORMER COUPLING AND USE OF NON-COAXIAL COILS

FIELD OF INVENTION

This invention relates to methods for non-destructive testing of prestressed concrete pressure pipes (PCPP). More particularly this invention relates to remote-field eddy current/transformer coupling (RFEC/TC), remote field eddy current (RFEC) and/or transformer coupling (TC) methods for testing prestressed concrete pressure pipes.

CROSS REFERENCE TO RELATED PATENT

This application is related to my earlier U.S. Pat. No. 6,127,823, issued 3 Oct. 2000, the disclosure of which is incorporated herein by reference. The RFEC/TC theory upon which the present invention is based is described in detail in the aforesaid prior patent.

BACKGROUND OF INVENTION

Non-destructive testing of large diameter steel pipes, such as natural gas pipelines, using magnetic-inspection techniques is well known in the art. Tools fitted with magnetic flux leakage (MFL) anomaly detectors embodying strong permanent magnets to magnetize the pipe wall to near saturation flux density are generally employed. Sensors, moving with the detectors, have signals induced by variations in the leakage fields and fluxes caused by such pipe-wall anomalies as internal or external corrosion, hard spots and so on, and including local variations in the magnetic permeability, often induced by local residual or stress concentrations. MFL anomaly detectors are, however, subject to problems caused by such things as noise, hostile operating environment, restricted power due to battery capacity and finite data storage capacity. Thick walled or small diameter pipes are more difficult to inspect by the MFL anomaly technique because there is frequently little space available inside such pipes for magnets compared to the relatively large pipe-wall cross sectional area to be driven into magnetic saturation. While this problem has been alleviated in recent years following the introduction of neodymium-iron-boron (NdFeB) permanent magnets, which have improved mechanical and magnetic properties and can produce higher usable flux densities than the earlier ferrite magnets and are mechanically stronger than cobalt-rare earth magnets, MFL anomaly techniques are generally limited to essentially direct contact inspection and are not generally suitable for indirect coupling through air or other materials or when there is appreciable sensor lift-off. Remote field eddy-current (RFEC) devices have been developed for these latter tasks.

RFEC devices incorporate transmit and receive coils and commonly use a solenoidal exciter coil, energized with low frequency ac or pulsed current (typically, 20–2000 Hertz), internal to and generally approximately coaxial with the longitudinal axis of the pipe to be tested. It has been found that the appropriate operating frequencies for non-ferromagnetic tubes, such as reactor pressure tubes are much higher, at about 10 kHz, than those suitable for winding ferromagnetic pipes, which are typically about, though preferably not at, 60 Hz. Low frequencies imply low scanning speeds. The detector coil, or array of detector coils, is placed adjacent the inside of the pipe wall and may be axially, radially or even circumferentially aligned. The exciter coil or coils are normally displaced longitudinally along the pipe from the detector coil by customarily about 2 to 3 pipe diameters (D). At this separation direct coupling inside the pipe between the exciter and detector is strongly attenuated by the eddy currents induced in the conducting pipe. The signal in the detector results principally from an indirect energy transmission path on the outside of the pipe. Field from the exciter diffuses through the pipe wall in the vicinity of the exciter, being attenuated and phase shifted in the process. Once on the outside, this energy radiates with relatively little attenuation. In the case of a ferromagnetic pipe, it tends to be guided preferentially in the axial direction.

Adjacent the remote detector coil or coils, the field on the outside of the pipe is greater than the field inside, which is generated largely by energy which diffuses back from the outside, again being attenuated and further phase shifted in the process. Anomalies anywhere in this through wall indirect energy transmission path will cause changes in the phase and amplitude of the received signals. Because the received signals are small, typically of the order of 10 $\mu v$ a phase sensitive synchronous detector or locked-in amplifier is incorporated to receive and amplify the signal.

While RFEC probes have now been used for many years for well casing inspection and more recently for heat exchangers and pressure tubes, the phenomenon is complex and defect responses are still not fully understood. Large diameter prestressed concrete pressure pipes (PCPP) have been used to convey water for many years and such pipes are frequently provided with a spirally wound high strength prestressing wire which prestresses the concrete before a top coating of mortar is applied. There are many types of PCPP. The cores of some may be just high strength concrete and are generally described as "no-cylinder" pipe, others, such as lined cylinder pipe (LCP) may have a thin metallic cylinder, preferably steel, or other metal such as iron or a nickel alloy, with a concrete core, often centrifugally cast, inside. Still others, such as the typically larger diameter embedded cylinder pipe (ECP), have an additional layer of concrete applied to the outside of the steel or alloy pipe before the prestressing rod, bar or wire is wound and a protective layer of mortar is impacted on top of the rod, bar or wire spiral. Some types of PCPP may be provided with both axially spaced reinforcing rods and spirally wound circumferential wires. As used in this specification, all of the above types of prestressed concrete pressure pipes are included within the definition "PCPP". Although generally high strength cold drawn steel prestressing wire is used, relatively lower strength hot or cold rolled bar or rod can also be used in some applications and these PCCP are generally described as bar wrapped. As used in this specification the term "prestressing wire" is to be construed to include both cold drawn wire and hot or cold rolled bar or rod. The surface of the prestressing wire and also the steel cylinder are often coated prior to winding with a highly alkaline slurry designed to promote the formation of a protective oxide film that will tend to inhibit corrosion of the steel.

While rupture of PCCP is relatively uncommon, nevertheless periodic inspection of water supply lines and the like, which have an expected service life of 50 years or more, would be advantageous in order to prevent expensive ruptures or other failures. Prior to my aforesaid earlier patent on the RFEC/TC, often loosely referred to as the "remote field" technique, there was no practical method for inspecting composite pipes, such as PCPP, and my earlier methods are susceptible to improvements.

OBJECT OF INVENTION

An object of the present invention is to provide improved methods for inspecting the steel prestressing wire or rods included in prestressed concrete pressure pipes (PCPP) embedded in concrete in situ. More particularly the improvements are directed to enabling the numbers and positions of broken prestressing wires to be quantified rather than the typical and much simpler objective of merely detecting the presence of broken wires.

SUMMARY OF THE INVENTION

By one aspect of this invention there is provided a method for detecting discontinuities in at least one prestressing wire in PCPP comprising:

passing an RFEC/TC remote field probe, comprising exciter means and detector means, each being adjacent an inner surface of said PCPP, through said PCPP; and energizing said exciter means with low frequency ac, so as to create an energy flow path, externally of said PCPP, between said exciter means and said detector means and a transformer coupling through said prestressing wire, inductively linking said exciter and detector means; and receiving a signal in said detector means, indicative of discontinuities in said prestressing wire, comprising at least a portion of indirect transformer coupling energy linking said exciter means and said detector means.

Many variations are possible and are needed to suit different pipe sizes and designs, different pipe and pipeline construction methods and materials properties. A key feature of the technique is that the through-wall signals obtained from breaks in the prestressing wire must be, at least, a detectable fraction of the direct internal coupling between the exciter and detector(s). This condition may be obtained by sufficiently separating the exciter means and detector means axially and/or radially and/or circumferentially or otherwise diminishing the natural direct coupling between the exciter(s) and detector(s) to achieve this remote field condition and, in this case, is simplified or relaxed relative to simple traditional RFEC probes by the transformer coupling effect which amplifies the response from the wires and other conductors external to the steel cylinder considerably. The remote field condition may often be most easily satisfied in large diameter PCPP using approximately coplanar but diametrically well separated exciter and detector coils. But in small diameter PCPP, axial separation, and therefore longer tools, may be needed. Other methods, well known to those skilled in the art, include:

the use of shields between the exciter and detector(s), as described in D. L. ATHERTON, W. CZURA AND T. R. SCHMDT, "FINITE ELEMENT CALCULATIONS FOR Shields in Remote-Field Eddy Current Tools", Materials Evaluation, Vol. 47 No. 9, 1084–1088, September. 1989, and in E. von Rosen and D. L. Atherton, "Effect of Shielding and Exciter Coil Tilt on the Remote-Field Effect", Materials Evaluation, Vol. 51, NO. 1 66–71, January. 1993;

the use of high permeability magnetic cores, such as ferrite, in the detector(s) and/or exciter(s); the sizes, shapes, orientations and alignments of the exciter and detector coils relative to each other and/or the pipe axis so as to reduce the direct internal coupling between the exciter and detector(s);

the use of multiple, including differentially connected exciters and/or detectors so arranged as to reduce the coupling between them; or the use of electrical feedback to the detector(s) of a suitably phase shifted and attenuated or amplified sample of exciter current, again so as to reduce or null the effective direct coupling between exciter and detector; or combinations of these techniques.

Specially shaped, non-coaxially wound coils may be used such as the use of elliptically shaped exciter coils which enable larger area exciter coils to be passed through the typically two foot or smaller diameter man holes which may be the only means of access to large pipes, even those with diameters greater than twenty foot. Specially shaped detector coils, for example those with arcuate segments may be desired in order to help ensure close coupling to the PCPP. Other detectors have been and may be used including but not limited to Hall probes, magnetoresistive or GMR probes, magnetic read heads, rotating, vibrating or scanning coils, fluxgate or proton precession magnetometers depending on such considerations as required range, sensitivity, resolution, size, frequency response, cost, ruggedness and reliability.

Optimizing the detailed structure and configuration of an RFEC/TC TOOL IS a complex engineering compromise amongst many additional competing requirements, considerations and effects including:

the choice of frequency and sampling rates, which affect, amongst other factors, scanning speed, signal amplitude, break signal resolution;

discrimination between break signals and other effects and also between nearby regions with breaks and the traditional, but unreasonable, desire for linearity of response;

the mechanical design of the tool which influences such factors as tool mass, water resistance, stability, reliability, ride quality, ease of assembly and reassembly;

the possible use of differentially connected detectors, which are frequently used in non-destructive testing to enhance anomaly signal and flaw detection although, in this case, they tend to complicate analysis to determine the numbers of broken wires;

optimization of signals not only from the centre lengths of pipes but also from near the ends of pipes and near joints between pipes;

optimizing the amount of data actually measured and recorded so as to provide just that which is useful, particularly with regard to the ease and speed with which it can be analyzed and used to generate accurate and useful reports on pipeline condition. For example this implies designing to minimize the effects of the relative circumferential positions of breaks with respect to the exciter(s) and detector(s);

optimal choice and selection of batteries, on board power generation or external supply; also traction systems for drawing, driving or passing the tool through the pipe; tape, DISLLT; removable disk, CD, solid state or other data recording, storage and backup systems; odometers or non-contact distance or position measuring or logging devices; and scanning the coils, simultaneously or relatively, either whilst the tool itself is moving or stationary.

It will be further appreciated that not only may and do pipes differ between pipelines in diameter and type of pipe, such as lined cylinder pipe, embedded cylinder pipe, bar wrapped pipe and no cylinder pipe but also, along even a single short line, for many reasons including:

hydrostatic pressure which typically varies with distance, elevation and flow along a line;

the pitch of the prestressing winding and the number of layers or its mass per unit length of pipe, which are adjusted by design to use different pipe classes for different locations;

variations in the pitch of the prestressing WINDINGS due to manufacturing processes;

variations in the details of the joints between pipes such as bell and spigot joints with and without steel end rings, the use of single or multiple gaskets, welded joints and sleeve joints;

the use of shorting strips on the prestressing winding and bonding between pipes in order to enable cathodic protection in potentially corrosive soil conditions; and the gauge of the wire and cylinder and, above all, variations in the magnetic properties of the steel cylinder which are greatly affected by residual, line pressure and bending stresses. For example residual stresses, due often to manufacturing processes including heat treatments and rolling, can cause large changes in permeability, magnetic anisotropy and easy axis over ranges of as small as a few millimetres over the surface of the steel cylinder and on an even smaller scale through its thickness; and, since pipes are normally buried, the depth of soil cover, the presence of tramp iron in the ditch or proximity to power lines or cables, other pipelines or sources of interference or pick up.

All these factors can and do affect the background and break signal responses and should therefore be taken into consideration when interpreting such signals. Where details of the design, manufacturing processes and materials properties are known and well understood those particularly expert in the state of the art can make calculations to estimate the effects of changes in these parameters on signals. The calculations needed are complex and involve combinations of eddy current skin effect approximations, Bessel function evaluations, finite element numerical calculations, coupled circuit electrical analysis, anomalous source signal models for wire breaks, Green's function analysis and sophisticated quasi three dimensional representation using, possibly, video clips or cartoons to display results since all the field vectors and derived quantities are time varying. Skills in performing such calculations are unusually valuable since test or calibration pipes or lines are typically much more expensive and less readily available than in most applications of non-destructive inspection and, furthermore, there are often significant differences between the pipes in test or calibration lines, as explained above, and between pipes in a line. The ability to calculate or estimate corrections for these differences is therefore of great importance.

The time varying signals may be measured and recorded, using either analogue form or, after conversion, in digital form, as in phase and quadrature or amplitude and phase representations of any or all of the axial, radial and circumferential or total fields, flux densities or derived quantities including induced voltages, differential or absolute values and displayed as Cartesian or polar plots, time or distance logs or using many derived forms. In practice special signal processing techniques may be used to enhance displays for the purpose of discriminating break signals from other signals such as those due to joints, variations in the permeability of the steel cylinder, concrete and slurry composition and properties, the effects of moisture and so on.

Suitable electronic circuitry for processing the relatively small induced signals in the detector coils or other sensors is well known to those skilled in the art and may include, although is not limited to, combinations of the following:

Preamplifiers, oscillators, power or audio amplifiers, phase sensitive detectors, lock-in amplifiers, phase lock loops, heterodyning systems, notch, low pass and band pass filters, digital signal processing chips, voltage controlled oscillators, multipliers and other electronic devices and circuits.

Whilst almost all of these functions can now be achieved using either analogue or, subsequent to conversion, digital circuitry, the final storage and backup stages are now preferably in digital format using magnetic tape, disks, (removable) hard drives, CDs or solid state memories, such as flash cards.

DETAILED DESCRIPTION OF PREFERRED EMBODIMENTS

Figure 1:
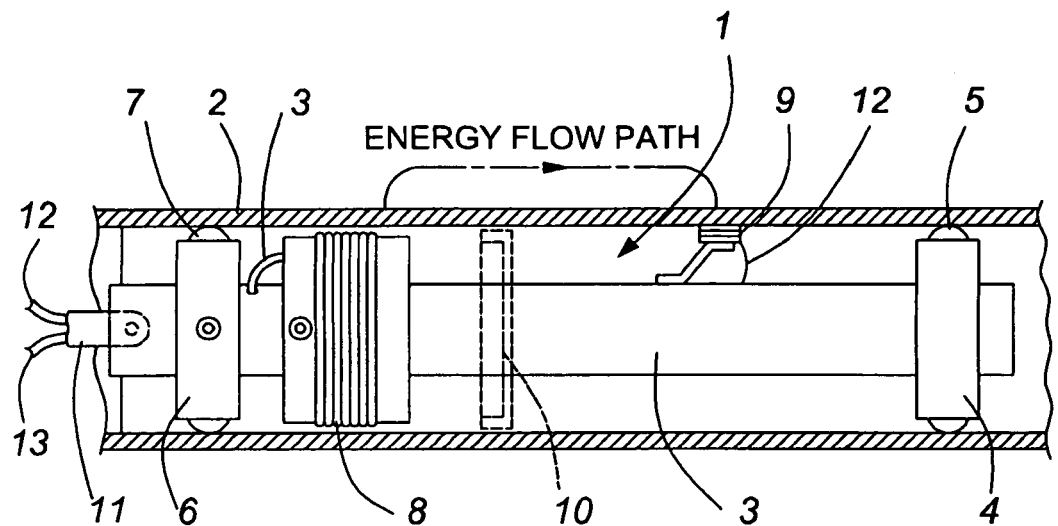
FIG. 1 is a cross sectional view of a simplified traditional RFEC probe contained within a cylinder.

An example of a simplified traditional RFEC field probe 1 in an electrically conducting metal tube, pipe or cylinder 2 is shown in FIG. 1, and comprises a cylindrical supporting body 3 having a forward carriage 4 having wheels 5 for rolling engagement with cylinder 2 and a rearward carriage 6 having wheels 7 for rolling engagement with cylinder 2, mounted at respective ends thereof. Other mounting means such as skids, brushes, cups or discs may be employed. Intermediate carriages 4 and 6 there is provided a solenoidal exciter coil 8 or coils which may be coaxial to the pipe and normally coaxially wound, and a detector coil 9 or circumferential or axial array of detector coils 9 which may be axially displaced from coil 8 by about two pipe diameters. Single or multiple exciters displaced and oriented axially, radially or circumferentially may be used with similar, opposed or different drives and may have different sizes and shapes. Single or multiple detectors displaced and oriented axially, radially or circumferentially or combinations thereof may be used with similar or opposed connection and may have different sizes and shapes. Optionally, one or more shields 10 are provided between coils 8 and 9. A drive rod, cable or wire 11 is provided adjacent carriage 6, which rod may be a hollow rod to carry signal cables 12 and a power cable 13.

As described hereinabove, when exciter coil 8 is energized with low frequency (20–200 HZ) ac or pulsed current a magnetic field is generated and diffuses through the pipe wall in the vicinity of the exciter, being attenuated and phase shifted in accordance with eddy current principles. Multi (generally harmonically related) frequency operation facilitates discrimination between signals due to flaws such as corrosion pits or broken wires and other anomalies such as support plates or joint rings, cylinder irregularities, nearby pipes, external tramp iron or other reflectors or re-transmitters. Once on the outside of the cylinder, this energy radiates with relatively little attenuation and, with a ferromagnetic cylinder, tends to be guided preferentially in the axial direction along the outer wall since low frequency magnetic fields impinge nearly radially on the wall to give a predominantly axial Poynting vector. In the remote field region, the field on the outside of the pipe may be greater than the field inside, which is generated partly by energy which diffuses back from the outside, again being attenuated by the circumferential eddy currents induced in the pipe's wall and further phase shifted in the process. Anomalies anywhere in this external indirect energy transmission path will cause changes in the phase and amplitude of the signal received at the detector coil 9. The received signal is carried by cable 12 to a phase sensitive detector or lock-in amplifier (not shown).

Figure 2A:
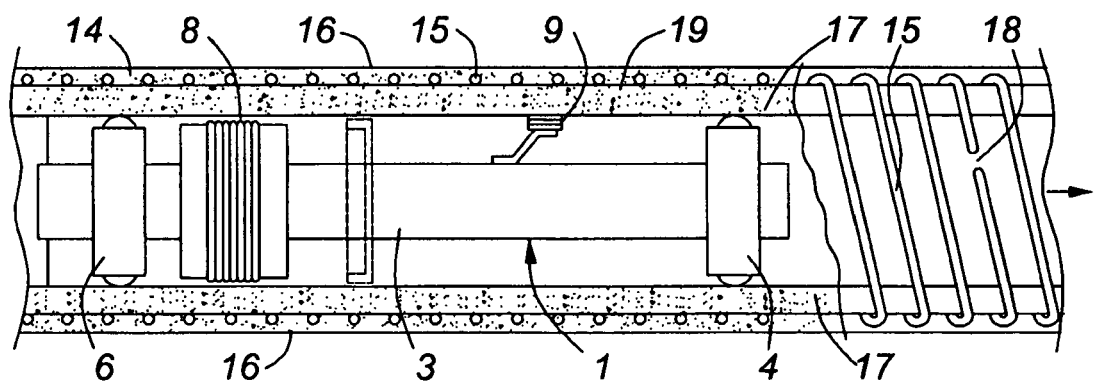
FIG. 2A is a schematic side view of a prestressed pressurized concrete pipe according to the invention, which pipe lacks the steel cylinder otherwise present in FIG. 2.
Figure 2:
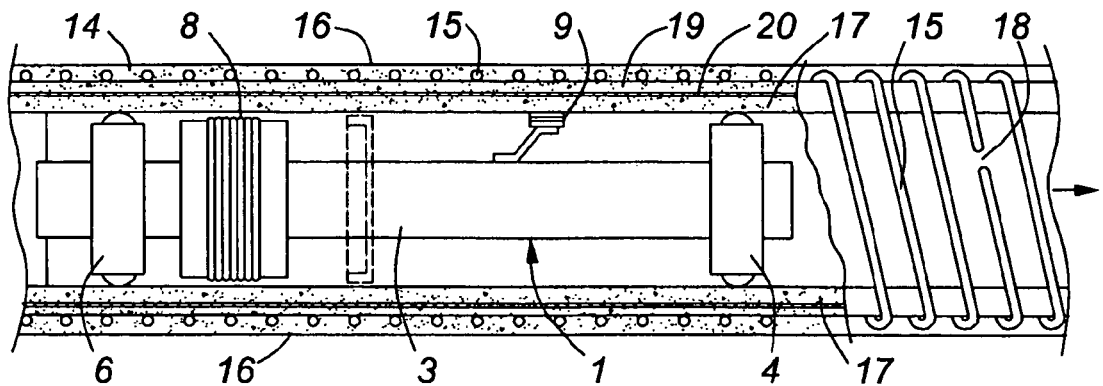
FIG. 2 is a side view of a wire wound prestressed concrete pressure pipe, partially in section and containing an RFEC/TC tool.
Figure 3:
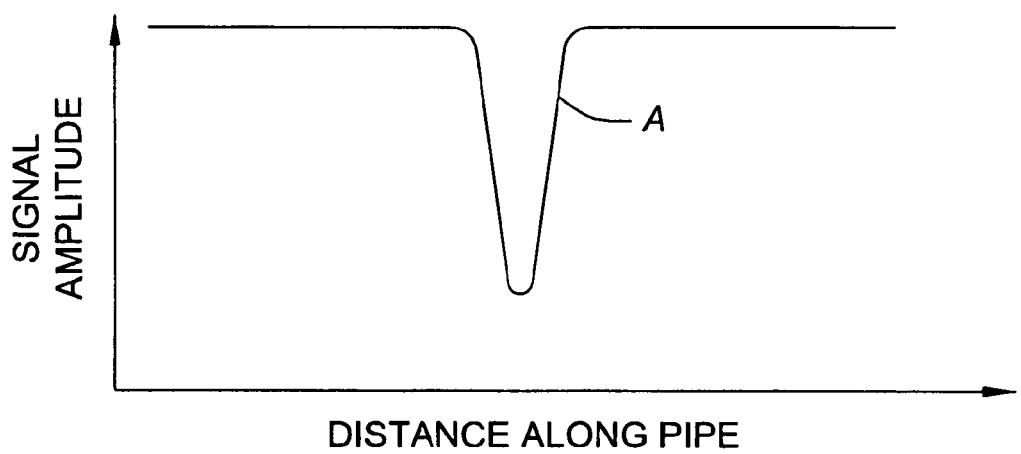
FIG. 3 is a log illustrating the amplitude of processed received signal relative to the axial position of an RFEC/TC probe in the cylinder.

FIG. 2 shows an RFEC/TC probe 1 in an embedded cylinder prestressed concrete pressure pipe 16. A concrete core 17 is cast on the inner wall of a thin metallic cylinder 20. An outer concrete core 19 is also cast onto the outer wall of the steel cylinder 20. A high strength steel prestressing wire 15 is then wound on spirally under high tension and a protective mortar coating 14 applied. If desired, one or more additional prestressing wires, not shown, may be added. Wire 15 is a generally continuous spiral, which may however contain splices, but if later corrosion causes even a single break 18 in one turn thereof, as probe 1 is advanced in the direction of the arrow shown in FIG. 2 an amplified read out signal due to a change in the electromagnetic field at the detector may be observed, as shown in the idealized graph of FIG. 3, in relation to the position of probe 1 in cylinder 16. Preferably exciter coil(s), 8, and detector coil(s) 9 are approximately coplanar and displaced radially and/or circumferentially so as to ensure that the indirect through transmission transformer coupling to the prestressing winding is at least a significant fraction of the direct coupling between the exciter and detector.

Optionally a high permeability core, using materials such as ferrite, Metglass, permalloy or mumetal may be used in the detector and/or exciter coil(s) to enhance the signals. Preferably, but not essentially, the exciter coil(s) are elliptical in shape so as to facilitate passage of coils of greater area through a standard access manhole in the cylinder and the detector coil(s) are arcuate with the arc proximal to the inner surface of the pipe so as to also enhance coupling to the prestressing winding. As the probe approaches the defect/break 18, the signal amplitude changes abruptly as detector coil 9 traverses the defect 18. It has been found that the change in signal A occurs as detector 9 is adjacent the specific turn of wire 15 containing defect 18. It is not necessary for coil 9 to be circumferentially adjacent defect 18 in order to generate a signal change. It will be appreciated, therefore, that a defect in the spirally wound wire can be detected by a pass of the probe 1 through cylinder 14. Circumferential scanning or a circumferential array may also be used to assist in determining the circumferential positions of wire breaks.

The use of differential coils, i.e. two detector coils mounted in opposition to each other so as to enhance break detection, reduce noise and improve the output signal is also contemplated.

Currents, which are easily measurable, are induced in an encircling external coupling coil such as formed by the prestressing wire when the exciter is within it. The winding then acts as a solenoidal coil. This generates fields which can be received by an axial detector any time that both the exciter and detector are within the closed prestressing winding. A radial field detector will have an induced signal relatively close to the inside wall near the end of the winding, provided that the exciter is within it. If even a single turn of the winding is cut or corroded through, these signals from the additional strong transformer coupling can be changed. It has been confirmed experimentally that the axial field is indeed detected with large lift-offs.

These signals are, of course, in addition to RFEC signals from cylinder joints, irregularities in the magnetic properties of the steel cylinder, tramp iron in the ditch in which the pipeline is buried, etc.

Figure 4:
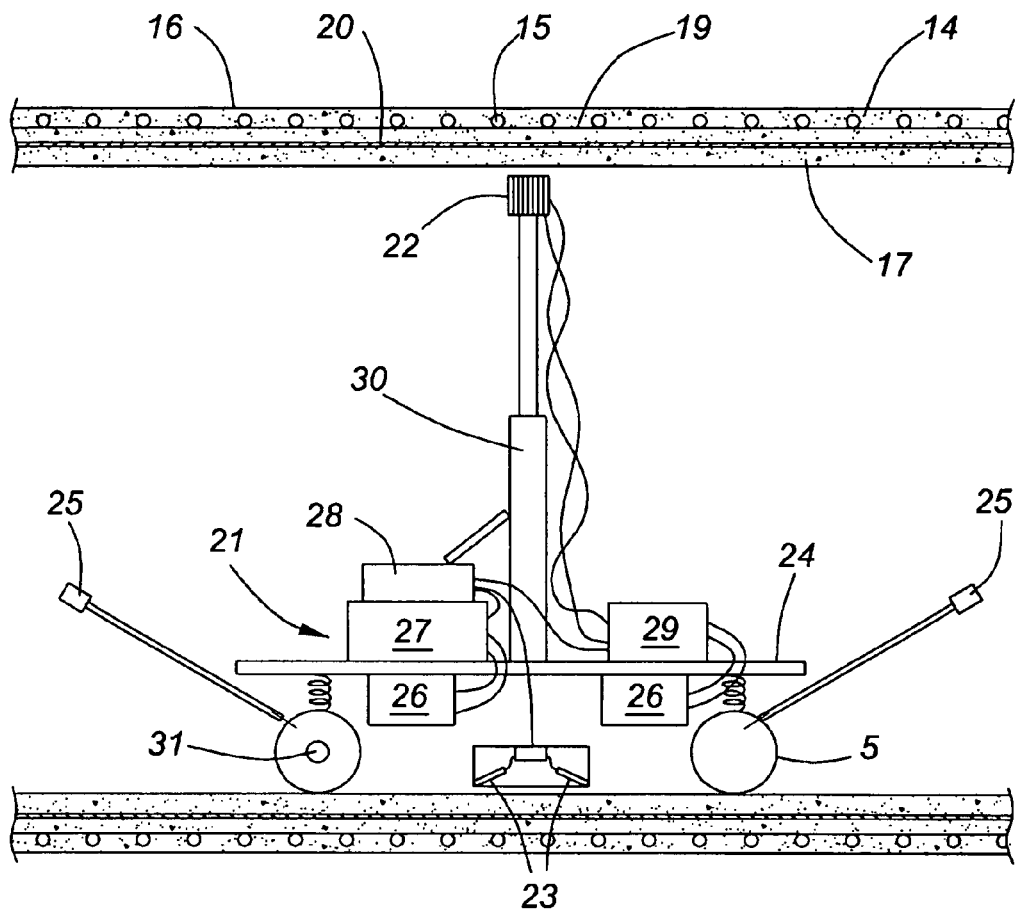
FIG. 4 is a schematic diagram of one embodiment of an apparatus to detect breaks in the prestressing wire in PCPP.
Figure 4A:
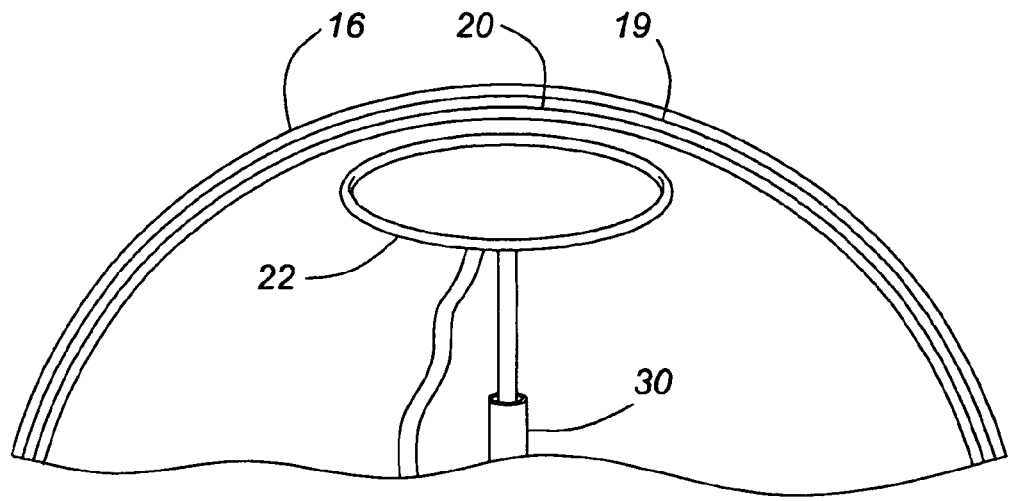
FIG. 4A shows a detail end view of a portion of FIG. 4 indicating the elliptical shape of the exciter coil 22.
Figure 4B:
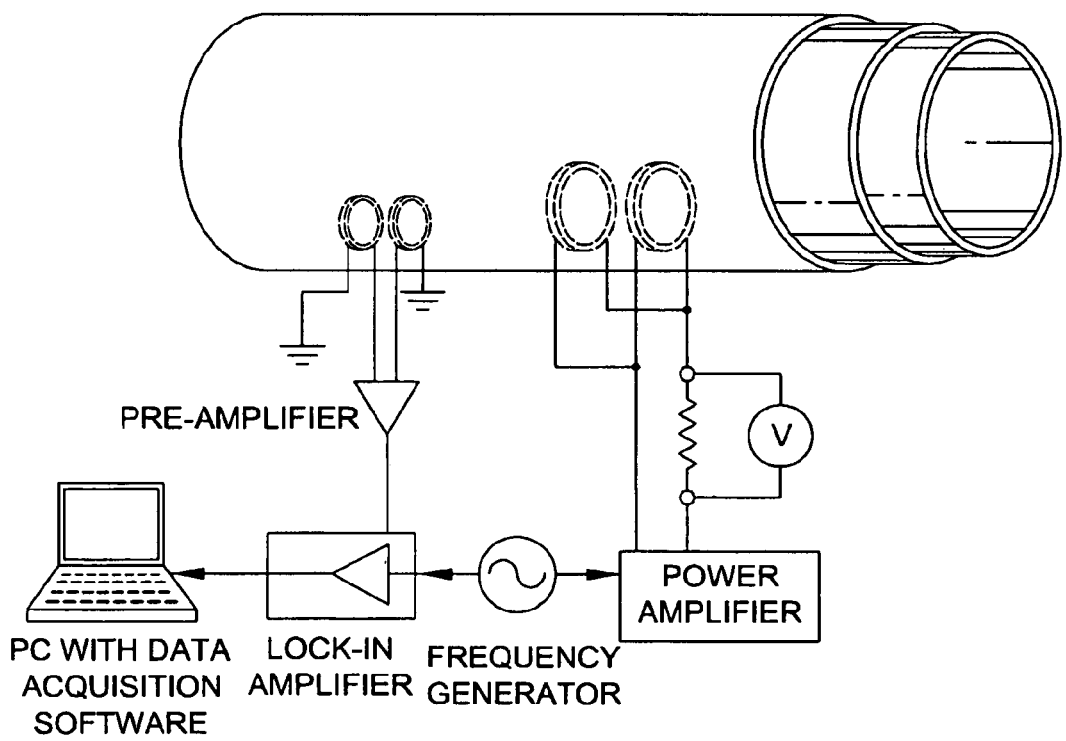
FIG. 4B shows a detail of the dual pickups 23 of FIG. 4 attached to a preamplifier.

FIG. 4 shows an example of an apparatus 21 used to generate the sinusoidal exciter field and to detect, amplify and record the RFEC/TC signal in pipes of the type described with reference to FIG. 2. In early tests operating frequencies of 140 Hz in a 600 mm pipe, and 190 Hz in a 400 mm diameter pipe were used. A current of 0.280 A was delivered to a 150 mm diameter, 1000 turn solenoidal exciter coil 22. Small diameter detector coils 23 were used to measure both the axial and radial field components. The exciter and detector coils were mounted on a wheeled cart 24, having a handle 25 at each end thereof to facilitate pulling. Batteries 26, data acquisition modules 27, computer 28 and power amplifier 29 were mounted on the cart 24. The exciter 22 was mounted on an extendible telescopic mast 30, which in turn was mounted on cart 24. An odometer 31 mounted on and driven by one of the wheels 5 was used in order to indicate axial displacement. The detector 23 was initially positioned 1.2 m away from the exciter coil 22, corresponding to three pipe diameters in the 400 mm pipe. This ensured that the apparatus operated in the remote field region. The remote field condition can also obtained using approximately coplanar exciter and detector at approximately opposed diametric positions in the pipe, as shown in FIG. 4, and in many other ways as detailed above. For axial field measurements the detector coil lift off from the inside of the concrete core was typically 90 mm but axial signals are relatively insensitive to lift off- and as much as 200 mm was used successfully. The lift off was reduced to 25 mm or less for radial field scans since, with increasing lift off, the radial amplitude decreases rapidly and the signal was soon lost in background noise.

The detector amplitude and phase were sampled at 20 Hz, giving adequate resolution to discern breaks in the prestressing wires, or the location of pipe joints. The RFEC/TC tool was pulled through the PCPP with typical scan speeds of 20 m/min, but rates as high as 35 m/min have been tested with little or no loss in resolution.

In the field, 6–7 m long pipes are joined or placed together to create A supply line. In many lines each pipe has a male spigot and female bell joint rings to permit a tight seal. Cutting a 400 mm PCPP and reversing the parts to join the male and female ends simulated such a joint. An insulating layer was inserted in the joint. The varying conductances between the prestressing winding, which in these lined cylinder pipes is wound directly onto the cylinder, and the local variations in the magnetic permeability of the cylinder cause irregularities in the background signal so the results are usually processed to reduce the influence of these variations.

The combination remote field/transformer coupling (RFEC/TC) technique described herein can detect even a single break or corrosion causing an open circuit in the prestressing wire used in PCPP. The method exploits the through wall RFEC characteristics to monitor the prestressing wire in the indirect energy transmission path external to the steel cylinder within the PCPP. There must therefore be sufficient axial and/or radial AND/OR circumferential distance between exciter and detector coils to ensure the remote field condition. The indirect energy path external to the cylinder is greatly enhanced by the transformer coupling effect between the exciter and detector coils when the prestressing wire also forms a closed coil or coils, with both exciter and detector coils inductively linked to it. The prestressing wire winding then acts as a solenoid driven by the exciter coil. An open wire reduces this transformer coupling and is therefore readily detectable.

The use of axial field exciters and detectors enables large lift offs and relatively small diameter (low fill factor) exciter coils and consequently a larger variety of arrangements are possible for RFEC/TC tools than for conventional RFEC tools where exciters with large fill factors and detectors close to the inner surface of the tube are strongly preferred.

Laboratory tests have generated good RFEC/TC logs at scanning speeds as high as 35 m/min. Voltage plane polar plots of the signal logs, developed for RFEC signal analysis, have shown that the signature traces from complete prestressing windings, broken windings and pipe joints can be distinguished by those specially trained or skilled in the art.

While this invention has been described with reference to the use of detector coils, it will be appreciated that ac Hall probes, magneto-resistors, FLUXGATE and possibly proton precession magnetometers may also be used as detectors.

I claim:

1. A method for detecting discontinuities in at least one prestressing wire in prestressed concrete pressure pipe (PCPP) with an embedded metallic cylinder having an inner surface and a central longitudinal pipe axis, comprising:
   passing an RFEC/TC remote field probe, comprising at least one exciter means and at least one detector means, each being adjacent the inner surface of said PCPP, through said PCPP;
   energizing said exciter means with low frequency ac, so as to create an energy flow path, externally of said metallic cylinder, between said exciter means and said detector means and a transformer coupling through said prestressing wire, inductively linking said exciter and detector means; and
   receiving a signal in said detector means, indicative of discontinuities in said prestressing wire,
   said signal comprising at least a portion of the signal arising from the transformer coupling linking said exciter means and said detector means and
   wherein at least one of said exciter and detector means comprises a non-coaxially wound coil.

2. A method as claimed in claim 1 wherein said at least one exciter means and at least one detector means each lie substantially in a common plane that extends transversely across said pipe at right angles to said central longitudinal pipe axis.

3. A method as claimed in claim 2 wherein said exciter and detector means are substantially diametrically opposed to each other.

4. A method as claimed in claim 1, wherein said low frequency ac is multi-frequency ac.

5. A method as claimed in claim 4 wherein said multi-frequency ac comprises harmonically related frequencies.

6. A method as claimed in claim 4 wherein said non-coaxially wound coil is an elliptical coil.

7. A method as claimed in claim 1 wherein said detector means are selected from the group consisting of detector coils, ac Hall probes, magneto resistors and fluxgates.

8. A method as claimed in claim 1, wherein said PCPP is a small diameter pipe and said exciter means and said detector means are axially displaced from each other.

9. A method as claimed in claim 1 wherein said PCPP is a large diameter pipe and said exciter means and said detector means are circumferentially displaced from being diametrically opposed to each other.

10. A method as claimed in claim 1, including the step of providing at least one of magnetic, electric and electromagnetic shields between said exciter means and said detector means so as to reduce natural direct coupling between said exciter and detector means.

11. A method as claimed in claim 1 wherein at least one of said detector and exciter means comprises a high permeability magnetic core.

12. A method as claimed in claim 1 wherein said detector means comprises a pair of differentially connected detectors.

13. A method for detecting discontinuities in at least one prestressing wire in a no-cylinder prestressed concrete pressure pipe (PCPP) having an inner surface and having a central longitudinal pipe axis comprising:
   passing an RFEC/TC remote field probe, comprising at least one exciter means and at least one detector means, each being adjacent the inner surface of said PCPP, through said PCPP;
   energizing said exciter means with low frequency ac, so as to create an energy flow path externally of said inner surface of said PCPP between said exciter means and said detector means and a transformer coupling through said prestressing wire, inductively linking said exciter and detector means;
   receiving a signal in said detector means, indicative of discontinuities in said prestressing wire, said signal comprising at least a portion of the signal arising from the transformer coupling linking said exciter means and said detector means and
   wherein at least one of said exciter and detector means comprises a non-coaxially wound coil.

14. A method as claimed in claim 13 wherein said at least one exciter means and at least one detector means each lie substantially in a common plane that extends transversely across said pipe at right angles to said central longitudinal pipe axis.

15. A method as claimed in claim 14 wherein said exciter and detector means are substantially diametrically opposed to each other.

16. A method as claimed in claim 13, wherein said low frequency ac is multi-frequency ac.

17. A method as claimed in claim 16 wherein said multi frequency ac comprises harmonically related frequencies.

18. A method as claimed in claim 13 wherein said detector means are selected from the group consisting of detector coils, ac Hall probes, magneto resistors and fluxgates.

19. A method as claimed in claim 13, wherein said PCPP is a small diameter pipe and said exciter means and said detector means are axially displaced from each other.

20. A method as claimed in claim 13 wherein said PCPP is a large diameter pipe and said exciter means and said detector means are circumferentially displaced from being diametrically opposed to each other.

21. A method as claimed in claim 13 wherein at least one of said detector and exciter means comprises a high permeability magnetic core.

22. A method as claimed in claim 13 wherein said detector means comprises a pair of differentially connected detectors.

* * * * *